United States Patent [19]

Thompson et al.

[11] Patent Number: 4,628,468

[45] Date of Patent: Dec. 9, 1986

[54] METHOD AND MEANS FOR DETERMINING PHYSICAL PROPERTIES FROM MEASUREMENTS OF MICROSTRUCTURE IN POROUS MEDIA

[75] Inventors: Arthur H. Thompson; Alan J. Katz; Christine E. Krohn, all of Houston, Tex.

[73] Assignee: Exxon Production Research Co., Houston, Tex.

[21] Appl. No.: 599,842

[22] Filed: Apr. 13, 1984

[51] Int. Cl.$^4$ .................. H01J 37/26; H01J 37/29; G01V 1/40

[52] U.S. Cl. .................. 364/556; 356/445; 364/422

[58] Field of Search .......... 250/310; 324/376, 377; 356/445; 73/153; 364/422, 556

[56] References Cited

U.S. PATENT DOCUMENTS

| | | | |
|---|---|---|---|
| 2,912,165 | 11/1959 | Poland | 364/422 |
| 2,942,176 | 6/1960 | Brownscombe et al. | 324/376 |
| 3,549,263 | 12/1970 | Osawa et al. | 356/445 |
| 3,866,044 | 2/1975 | Grund | 250/310 |
| 3,908,079 | 9/1975 | Worthley | 364/556 |
| 4,030,837 | 6/1977 | Kojima et al. | 356/445 |
| 4,361,110 | 11/1982 | Holmes | 356/445 |

OTHER PUBLICATIONS

"Three Morphological Mathematical Studies in Engineering Geology," Bulletin de l'Association Internationale de Geologie de L'Ingenieur, No. 13, pp. 89-97, by E. N. Kolomenski and J. Serra (original in French, with English translation attached).

"Random Walks on Fractal Structures and Percolation Clusters," J. Physique-Lettres, 44, pp. L13-L22, by R. Rammal et al.

"Lattice Dynamics, Random Walks, and Nonintegral Effective Dimensionality," J. Math. Phys., 23, 1688-1692, by B. D. Hughes and M. F. Shlesinger.

"Solvable Fractal Family, and Its Possible Relation to the Backbone at Percolation", Phys. Rev. Lett. 47, pp. 1771-1774, by T. Gefen et al.

"On a Relation Between Percolation Theory and the Elasticity of Gels", J. Physique Lettres, 37, pp. L1-L2, by P. G. deGennes.

F. W. Preston et al., 6th Annual Computers and Operation Research in Mineral Industries Symposium Reprint (1966), pp. 1-20.

F. W. Preston et al., Random Processes in Geology, D. F. Merriam (Ed.) (Springer-Verlag New York/Germany 1976), pp. 63-86.

C. Lin, "Microgeometry I: Autocorrelation and Rock Microstructure," International Assn. of Math. Geol. Journal, 14, pp. 343-370 (1982).

J. D. Orford et al., Sedimentology, 30, pp. 655-668 (1983).

J. Serra, Image Analysis and Mathematical Morphology, pp. 152-158 (Academic Press, New York 1982).

J. Chermont et al., J. Mater. Science, 14, 509-534 (1979).

B. H. Kaye, Powder Technology, 21, pp. 1-16 (1978).

Primary Examiner—Errol A. Krass
Assistant Examiner—Edward R. Cosimano
Attorney, Agent, or Firm—A. A. Equitz

[57] ABSTRACT

A method and apparatus for predicting pore-dependent physical properties of a microporous solid from measurements of the geometric statistical characteristics of the solid. In a preferred embodiment, the method involves a microscopic determination of the number of geometric features of the pore surface as seen by microscopy performed at several levels of magnification. The fractal dimensionality of the pore space and the range of length scales over which the geometric features of the solid obey a self-similar size distribution are determined. From the measured data, such properties as the porosity, electrical conductivity, and permeability are determined. The method may be performed to determine pore-dependent physical properties of various microporous solids, including reservoir rock, heterogeneous catalyst materials, and electrochemical electrodes. The method may be performed automatically using a specially designed measurement system comprising a microscope or microdensitometer and signal processing means including a computer.

43 Claims, 7 Drawing Figures

METHOD AND MEANS FOR DETERMINING PHYSICAL PROPERTIES FROM MEASUREMENTS OF MICROSTRUCTURE IN POROUS MEDIA

FIELD OF THE INVENTION

This invention relates to methods and means for determining pore-dependent properties of a microporous solid by measuring pore microstructure. More particularly, the invention relates to methods and means for determining pore-dependent properties, such as porosity, conductivity, and permeability, of a microporous solid from measurements of the geometrical statistical properties of the pore surface of the solid.

BACKGROUND OF THE INVENTION

Many commercially significant applications exist for methods by which the physical properties of a microporous solid may be predicted from measurements of the pore geometry of a sample of the solid. In petroleum geophysics, for example, the maximum hydrocarbon content of reservoir rock may be estimated from measurements of the rock porosity. The fraction of the pore volume of reservoir rock occupied by water (the "water saturation") may be estimated from measurements of the rock porosity and electrical conductivity. Any method or apparatus for improving the accuracy or speed of porosity and saturation measurements would thus enhance the efficiency and reliability of reservoir description and evaluation. Any method for accurately predicting rock permeability from measurements of pore geometry would also enhance the reliability of reservoir description and evaluation. It is an object of the present invention to provide such improved methods and means for enhancing the reliability of reservoir description and evaluation.

The present invention may also be applied to predict a variety of physical properties of many types of microporous solids other than reservoir rocks. For example, the invention may be applied to predict the porosity, permeability, conductivity, and diffusivity of fluids in heterogeneous catalyst materials. For another example, the invention may be applied to predict the ionic conductivity of porous electrochemical electrodes.

Established techniques in the fields of well logging and core analysis use empirical correlations between pore volume (or pore geometry) and physical properties, such as ionic conductivity, of reservoir rock. These empirical correlations are based on the premise that the rock properties associated with pore fluids are ultimately related to the pore geometry. With this underlying premise, there have been numerous attempts to characterize pore and grain geometry in such a way that pore-dependent physical properties can be predicted from measurements of pore and grain geometry.

Most such pore and grain characterization methods are characterized by a single underlying principle: the pore space is modeled as a bundle of discrete, smooth-walled tubes with fixed or varying tortuosity, connectivity, and cross section. The smooth-walled tubes of the model may then be reduced to network models or treated as discrete elements in a mosaic partitioning of the pore space. Alternatively, the rock grains or pore space are modeled as a connected framework of line segments.

The physical measurements of pore or grain geometry carried out in performing this type of method typically involve determination of pore size distribution by mercury intrusion porosimetry, measurement of the pore aspect ratio, measurement of the internal surface area, extraction of the ellipticity of pore cross sections, counting the number and area of pores on grids of thin sections of rock, measurements of porosity by fluid displacement or Boyle's Law techniques, or characterization of rock grains by size (either volume or linear dimension, such as by sieving), ellipticity, and various shape factors.

Variations on the conventional grid technique of counting pore space area on thin sections of rock are suggested in F. W. Preston, et al., 6th Ann. Computers and Operation Research in Mineral Industries Symposium Reprint (1966), p. 1; F. W. Preston, et al., *Random Processes in Geology*, D. F. Merriam (Ed.) (Springer-Verlag New York/Germany 1976), p. 63; and C. Lin, "Microgeometry I: Autocorrelation and Rock Microstructure," International Assn. of Math. Geol. Journal, 14, pp. 343–370 (1982).

The Preston et al. papers, which develop a statistical description of a rock and its pore space, disclose digitizing a line across an image of a thin section of rock by assigning a $-1$ value for solid and a $+1$ value for pore space. The power spectrum of the digitized data is computed. At each point, a judgment is made as to whether a point is pore or solid so that a sharp boundary between the two is defined. The Preston, et al. method is very different from the present invention. The Preston, et al. papers do not suggest any method capable of detecting the structure observed in performing the present invention.

The Lin paper (referenced above) also suggests a method for characterizing pore space geometry by analyzing binary images of thin sections of rock. The Lin method is similar to the Preston, et al. method, with utilization of two-dimensional image statistics rather than one-dimensional statistics and computation of the auto-correlation function (closely related to the power spectrum) of the digitized data rather than the power spectrum of the data. Lin discloses generating the binary image by identifying areas of a scanning electron microscope image of a thin section as belonging either to pore space or grain space, in order to measure the correlations between a central rock grain (or pore space) and grains (or pores) at a distance from the central grain (or pore). Lin concluded that this method gave no information about anisotropy, connectedness, or correlations that significantly differed among rocks with very different transport properties. The Lin method, intrinsically different from that of the present invention, is unsuitable for measuring the structure (typically occuring at length scales smaller than on the order of 100 microns) of interest in the present invention. Indeed, the auto-correlation function, the Fourier Transform and the power spectrum of a thin section contain information about correlations between pore spaces that obscures the structural information of interest in practicing the present invention.

The use of various statistical methods to characterize individual rock grains is disclosed by J. D. Orford and W. B. Whalley, Sedimentology, 30, pp. 655–668 (1983). The Orford paper discloses using the fractal dimension (discussed below) to characterize the shapes of individual rock grains. However, the methods disclosed in the Orford paper are unsuitable for measuring the structure of an ensemble of rock grains as assembled in a rock structure. The Orford paper neither discloses nor suggests any method for measuring pore-dependent properties of a microporous solid.

The present invention differs from previously known pore and grain characterization methods in two basic respects. First, the present invention places central importance on the roughness or complexity of the pore surface, in a manner to be described in detail below. The geometric features measured according to the present invention typically have a range of sizes down to on the order of $10^{-2}$ microns or less. In contrast, the pore and grain sizes observed in the conventional measurements are typically larger than on the order of 10 microns. The conventional approximations treating pores and grains as smooth tubes or ellipses remove much of the structure observed in performing the present invention.

The second respect in which the present invention differs from conventional pore and grain characterization methods is that the present invention treats the statistics of the porous solid and its pore space as a whole. No effort is made, in practicing the present invention, to discretize the porous solid into component grains, or to divide the pore space into pores of defined average dimension. Rather, the present invention involves determining the statistical geometrical properties of the pore walls or the statistical properties of the pore space at length scales comparable to or smaller than the largest geometrical structure on the surface of the pore space.

Outside of the field of rock physics, mathematicians and physicists have developed new statistical descriptions of random media. B. B. Mandelbrot has coined the word "fractal" to describe many statistically random geometries found in nature. See *The Fractal Geometry of Nature* (Freeman, San Francisco, 1982) by B. B. Mandelbrot. An object possessing geometric features having a size distribution such that the number of features of size l per unit length is proportional to the size l raised to some power, p, is said to have a "self-similar" distribution of features and to be characterized by a "fractal geometry". The coast lines of islands and the perimeters of clouds are examples of fractal geometries in nature. The central goal of these researchers has been to precisely characterize geometrical properties such as the length of a coast line or the volume of a mountain range.

A variety of objects have been analyzed in terms of self-similarity or in terms of fractals. For example, the size distribution of clusters in thin metal films [see R. F. Voss, et al., "Fractal (Scaling) Clusters in Thin Gold Films Near the Percolation Threshold", Phy. Rev. Lett., 49, pp. 1441-1444 (1982); and A. Kapitulnik et al., "Percolation Characteristics in Discontinuous Thin Films of Pb", Phy. Rev. Lett., 49, pp. 1444-1448 (1982)] and the size distribution of clay particles in a clay sample [see J. Serra, *Image Analysis and Mathematical Morphology*, pp. 152-158 (Academic Press, New York 1982)] have been found to exhibit self-similarity. Self-similar behavior has also been observed in measuring the roughness of objects such as a fracture surface [see J. L. Chermont, et al., "Review Quantitative Fractography", J. Mater Science, 14, pp. 509-534 (1979)] and a single fine particle [see B. H. Kaye, "Specification of the Ruggedness and/or Texture of a Fine Particle Profile by its Fractal Dimension", Powder Technology, 21, pp. 1-16 (1978) and Orford and Whalley (referenced above)].

The procedures previously used in analyzing objects in terms of self-similarity are very different from the method of the present invention. One type of such procedure (employed, for example, by Voss et al. in the above-cited reference) involves measuring the perimeter versus the area of each of a plurality of distinct objects comprising a system. An inherent difficulty with this type of procedure is delineating the boundary of each object measured. Another type of procedure measures the length of a boundary of an object whose roughness is to be characterized, as a function of various selected finite step sizes. This may be accomplished by repeatedly performing a walk about the rough object with successively smaller step size, or by covering the boundary of the rough object with objects, such as circles, of decreasing size. In the latter procedure, known as "dilation", the length of the boundary is measured to be the area covered by the circles divided by the diameter of a single circle.

Another type of procedure (suggested by Serra in the above cited reference) involves scanning the surface of a clay sample, using an electron microscope scanner, to obtain a photograph of the sample at each of several magnifications. The intensity of each photograph along a line randomly drawn thereon is measured, and the covariance of each such intensity signal is computed. From each computed covariance function, a value representing the apparent number of clay particles intersected by the line drawn on the photograph, is calculated. Serra suggests a method for determining whether or not the size distribution of the clay particles exhibits self-similarity but does not suggest how pore-dependent physical properties of interest, such as porosity and electrical conductivity, may be determined. The Serra method relies on the assumption that the ratio of the apparent number of particles intersected by each line to the actual number so intersected does not substantially change as the magnification is changed and that the intensity of the signal does not change with feature size or with magnification. The Serra method requires manipulations, including the computation of covariance functions, which are avoided in practicing the method of the present invention. The present invention involves making microscopic measurements of a microporous solid to generate feature size distribution signals very different from any signal generated by the Serra method. Furthermore, the assumption that the signal intensity does not vary with feature size or magnification made in the Serra method is inconsistent with the intensity variations observed in practicing the present invention. Application of the present invention is not limited to specific cases in which the feature size is proportional to the intensity of the signal from the feature.

SUMMARY OF THE INVENTION

The present invention relates to methods and means for predicting pore-dependent physical properties of a microporous solid from microscopic measurements of the geometric complexity of the pore surface. The method involves a microscopic determination of the number of geometric features of the pore surface as seen by microscopy preferably performed at several levels of magnification. The number of features having a particular size is compared with the size of the counted features to determine certain geometric statistical characteristics of the measured solid.

If a power law relation exists for the geometric features, such that the number of features of size l per unit length is proportional to the size, l, raised to some power, p, then the pore space is characterized by a fractal geometry and various pore-dependent physical properties are predicted from the measured data. For example, the porosity, $\phi$, of the measured solid is determined by the relation $\phi=(l_1/l_2)^{3-D}$, where $l_1$ and $l_2$ respectively are the smallest and largest lengths at which the feature size distribution obeys the power law relation, and D is the fractal dimension of the pore space (D is determined from the measured power, p). The electrical conductivity, $\sigma$, of the solid may be determined by the relation $\sigma = \sigma_s + \sigma_w (l_1/l_2)^{3-D+\gamma}$, where $\sigma_w$ is the conductivity of fluid saturating the pore space, $\sigma_s$ is the electrical conductivity of the solid portion of the microporous solid (i.e., $\sigma_s$ is the electrical conductivity of the microporous solid when its pore space is filled with an electrically insulating substance), and $\gamma$ is another geometric statistical characteristic of the pore space, referred to herein as the clustering statistic. Similarly, other physical properties of the solid, such as permeability, are determined.

The method may be performed to determine physical properties of a variety of microporous solids, including reservoir rock, electrochemical electrodes, and heterogeneous catalyst materials. The method may be performed automatically using a specially designed system comprising a microscope and signal processing means including a computer.

DETAILED DESCRIPTION OF THE PREFERRED EMBODIMENTS

Figure 1:
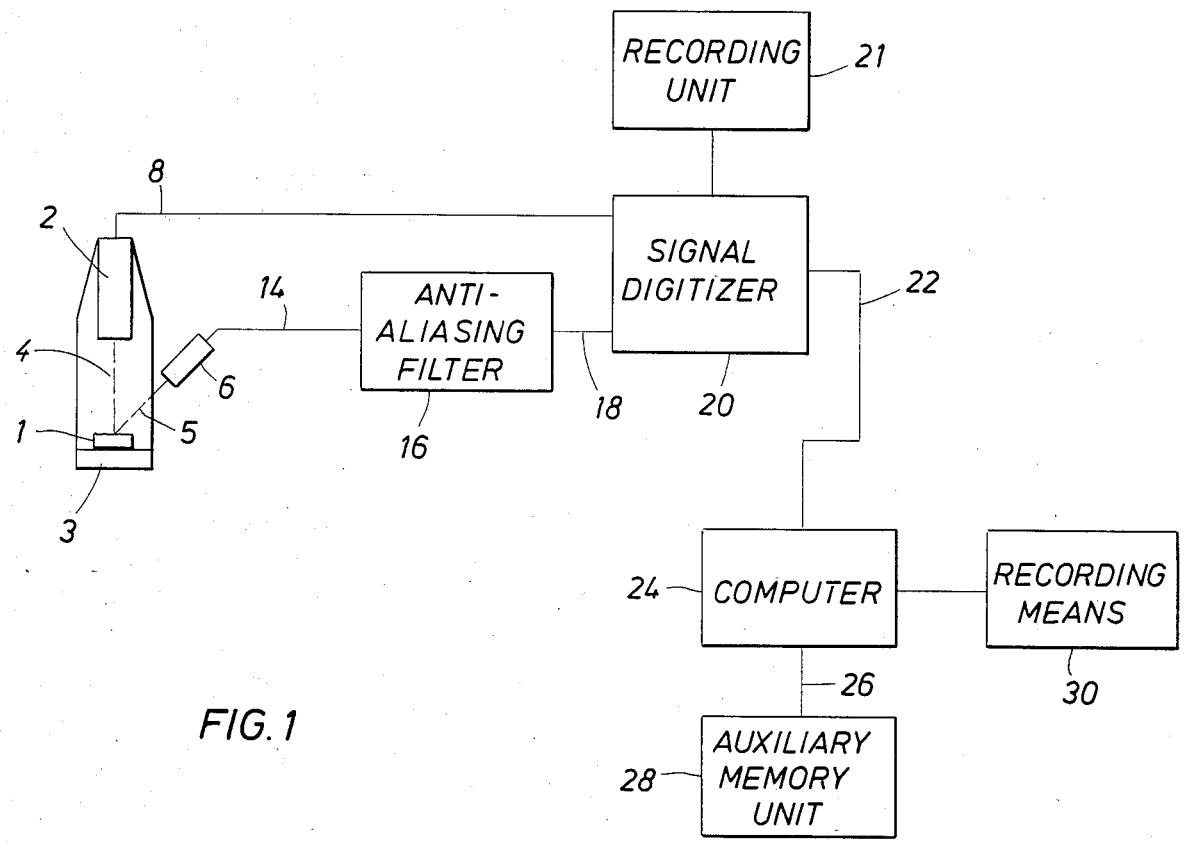
FIG. 1 is a schematic diagram of a preferred embodiment of the automated measurement system of the invention.

It is important to an understanding of the invention initially to explain the statistical notions underlying the invention. We have found that the pore space of a large class of microporous solids may be characterized as having a statistically random geometry known as a "fractal geometry." Such solids possess geometric features ("geometric feature" will be defined below) whose size distribution is such that the number of geometric features of size l per unit length is proportional to the size l raised to some power, p. Such a power-law feature size distribution will be referred to herein as a "self-similar" size distribution, and a solid possessing such a self-similar size distribution will be referred to as exhibiting "self-similarity."

For a solid exhibiting self-similarity, if N(r) is the number of geometric features of the solid per unit length have size "r", then N(r) is proportional to $r^{-D+2}$. We define D to be the Hausdorff dimensionality or fractal dimensionality. Throughout this specification the synonymous phrases "fractal dimension" and "fractal dimensionality" will be used interchangeably. We view the solid as an assemblage of geometric features satisfying a self-similar size distribution and the remaining unfilled space inside the solid (the pore space) as a complex, rough manifold. The geometry of the pore space, a fundamental physical property of the solid, may be characterized by such parameters as the fractal dimensionality D, and the minimum and maximum length scales over which the solid exhibits self-similarity.

The fractal dimension, D, behaves in many ways like a spatial dimension. For example, the dimensionality associated with the linear section of an isotropic, homogenous volume-filling fractal geometry of dimension D is simply D-2. This property permits exploitation of the geometric information contained in a linear trace obtained by scanning the surface of a self-similar solid with a microscope. For another example, the dimensionality associated with the planar section of an isotropic homogenous volume-filling fractal geometry of dimension D is simply D-1.

We have recognized that, having determined that a porous solid exhibits self-similarity over a range of length scales from $l_1$ (the smallest length at which self-similarity occurs) to $l_2$ (the largest length at which self-similarity occurs), and having measured the fractal dimensionality, D, certain pore-dependent physical properties of the solid may be calculated using the mathematics of fractals. For example, the porosity, $\phi$, is given by $\phi = (l_1/l_2)^{3-D}$.

Another fundamental statistic characteristic of the geometry of a self-similar solid is the clustering statistic, $\gamma$. The clustering statistic relates to the average size of clusters of geometric features having size l. For a given feature size, l, the average volume, $V_r$ (known as the "reduced volume"), of clusters containing geometric features of size l, is given by $V_r = (l_1/l_2)^\gamma (l_{nr}/l_1)^D$, where D is the fractal dimension, $l_1$ and $l_2$ respectively are the smallest and largest length scales at which the solid exhibits self-similarity, and $l_{nr}$ is the linear size associated with the volume available to a cluster containing geometric features of size l in the absence of clustering.

We have recognized that, having determined that a porous solid exhibits self-similarity over a range of length scales from $l_1$ to $l_2$, and having measured the fractal dimension, D, and the clustering statistic, $\gamma$, certain additional pore-dependent physical properties of the solid (such as permeability and electrical conductivity) may be calculated. For example, if the porous solid is a porous rock whose solid portion is substantially electrically insulating, the rock electrical conductivity $\sigma$ is given by $\sigma = \sigma_w (l_1/l_2)^{3-D+\gamma}$, where $\sigma_w$ is the electrical conductivity of fluid saturating the pore space. We shall discuss below the manner in which the electrical conductivity of a porous sample may be determined, in the general case that the sample has an electrically conducting solid portion.

FIG. 1 schematically illustrates a preferred embodiment of the automated measurement system of the invention. The system includes scanning electron microscope 2 which is capable of operating in a secondary electron mode at at least two selected magnifications. Scanning electron microscope 2 may be selected from those well known in the art. For example, a JEOL-35C Scanning Electron Microscope has been found suitable. Microporous solid sample 1 is placed on specimen stage 3 of scanning electron microscope 2 so that sample 1 may be scanned by scanning electron beam 4. The scanning path may be linear, or may have any other desired shape. Sample 1 may consist of any microporous solid. For example, sample 1 may be a portion of a microporous reservoir rock. A thin section of the sample need not be prepared. Rather, the cleaved surface of a sample may be directly scanned. In the event that the geometric features of a rock sample are to be measured, the surface of the sample may desirably be coated with a thin layer of gold. Secondary electron beam 5 is emitted from sample 1. Secondary electron photomultiplier 6 is provided for detecting secondary electron beam 5, and generating a time-dependent voltage output signal indicative of geometric features of sample 1 intersecting the projection of the scanning path on sample 1.

Photomultiplier 6 is coupled by cable 14 to the input of anti-aliasing filter 16. The output of anti-aliasing filter 16 is coupled by cable 18 to one input of signal digitizer 20. A gate output of scanning electron microscope 2, coupled by cable 8 to another input of signal digitizer 20, is used to trigger signal digitizer 20 at the start of each scan. Anti-aliasing filter 16 is a low-pass filter for preventing aliasing. Typically, most geometric features counted will have size close to that of the cutoff of filter 16. Accordingly, filter 16 should be transient free (that is, it should not have an oscillating impulse response function) and should have linear phase near the cutoff frequency. The response of filter 16 to a square wave should be smooth, without overshoots, which would be counted as extra features. Filter 16 should have linear phase near the cutoff frequency because nonlinear phase would result in a time shift for each feature which would vary for different frequency components, resulting in erroneous feature size measurements. Filter 16 may be selected from those commercially available. We have found that a Krohn-Hite RC low-pass analog filter (Model 40) is suitable.

Signal digitizer 20 digitizes the filtered voltage output signal to facilitate subsequent signal analysis. Signal digitizer 20 may be selected from those commercially available. We have found that a Hewlett-Packard HP-3437A voltmeter is suitable for use as signal digitizer 20 in some applications. Optionally, recording unit 21 is electrically coupled to signal digitizer 20 for recording the digitized voltage output signal. We have found that a Hewlett-Packard Model 5420 Signal Analyzer, which includes both a digitizing means and means for recording on magnetic tape the digitized output of the voltmeter, is suitable for use as both signal digitizer 20 and recording unit 21.

Processing the filtered and digitized signal in computer 24 involves computing the time derivative of such signal for purposes to be discussed below. In an alternate preferred embodiment, a conventional anti-aliasing filter replaces filter 16 and a digital filter having a transient-free, linear phase impulse response function is simulated numerically by the computer 24. In such an alternate configuration, computer 24 may both differentiate and filter the digitized signal in one step by convolving the digitized signal with the derivative of the digital filter impulse response function.

The output of signal digitizer 20 is coupled via cable 22 to computer 24. The digitized voltage output signal is analyzed in computer 24 in a manner to be discussed below. One or more auxiliary memory units 28 are coupled to computer 24 if the internal memory of computer 24 is insufficient to permit processing of the digitized data and storage of the processed data. We have found that a Tektronics 4054 computer with an auxiliary Trans Era 128 K bytes memory are suitable for use as computer 24 and auxiliary memory unit 28, respectively. Recording means 30 is coupled with computer 24 for recording the data processed in computer 24. Suitable recording means 30 may be selected from those commercially available.

In an alternate embodiment of the invention a signal image analysis system, selected from those commercially available, is employed for processing the output signal from scanning electron microscope 2. Signal image analysis systems suitable for use in practicing the invention include those which comprise a TV camera, a dedicated computer, and an interface between the camera and computer. The procedure to be described below for extracting desired statistical information from the output signal of the electron microscope may be performed automatically in such alternate embodiment by translating the procedure into a series of instructions for the computer, in a manner that will be apparent to those ordinarily skilled in the art of computer programming.

Figure 2:
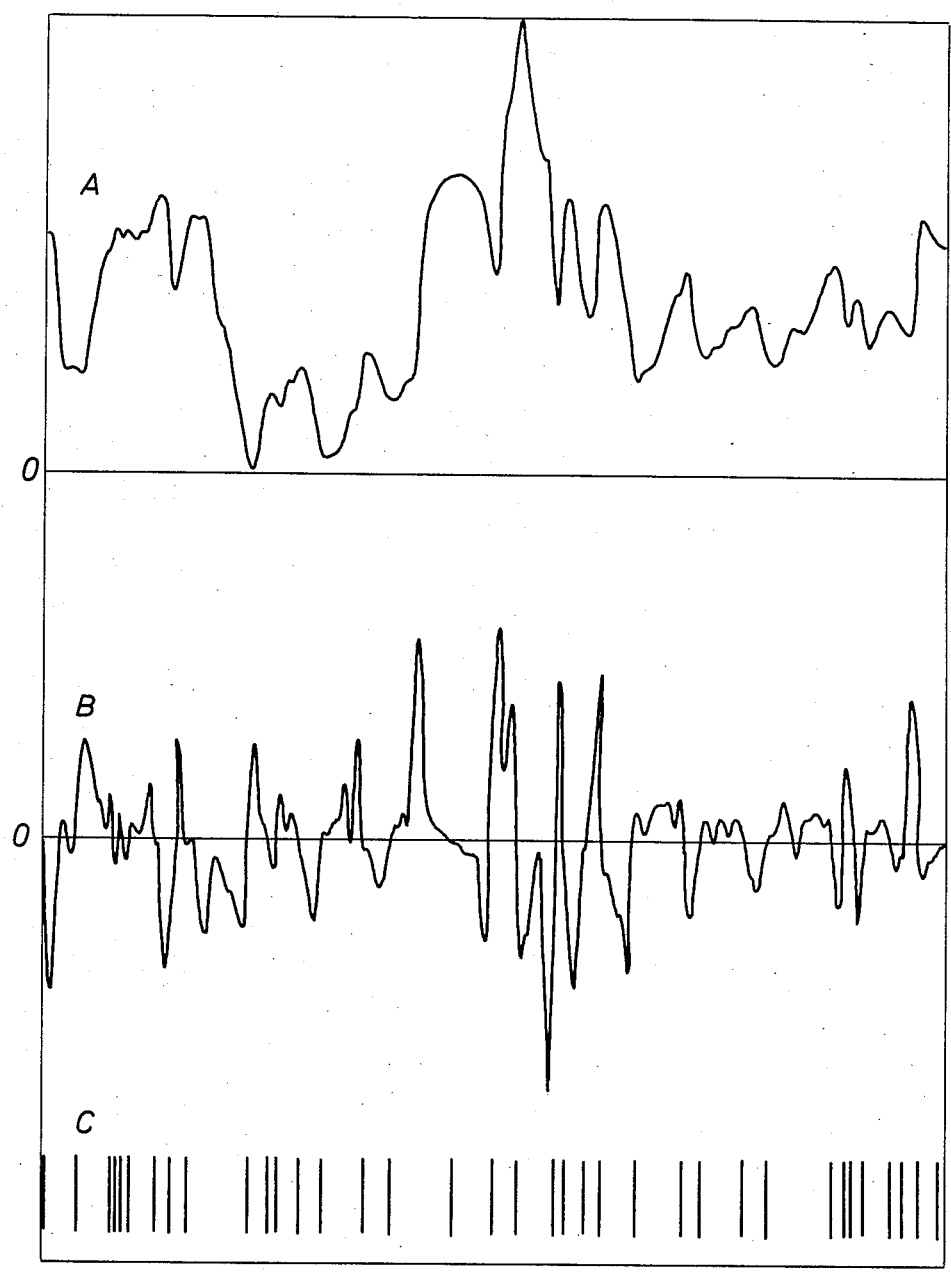
FIG. 2 is a set of three graphs showing several steps in analyzing the signal obtained by scanning a sample in accordance with the method of the invention. The unprocessed signal is denoted by reference letter A; the derivative of unprocessed signal A is denoted by reference letter B; and the locations of the zero crossings of signal B are denoted by reference letter C.

The invention may be more fully understood with reference to FIG. 2, a set of three graphs illustrating how a signal obtained by scanning a microporous solid may be analyzed in accordance with the invention. The distance away from the horizontal axis of each graph represents signal amplitude. The distance away from the vertical axis of each graph represents time elapsed during the step of scanning the sample with a microscope.

Signal A of FIG. 2 represents an unprocessed voltage output signal from photomultiplier 6 of scanning electron microscope 2. According to the invention, such a signal is analyzed to determine the number per unit length of geometric features of scanned sample 1 having a particular size. An unambiguous definition of a "geometric feature" of the sample as seen by scanning electron microscope 2 will be developed in the following paragraphs. Since the signal of FIG. 2A is obtained by scanning sample 1 along a scanning path using a microscope operated at a particular selected magnification, knowledge of the velocity at which the scanning occurs (i.e., the rate at which electron beam 4 is translated relative to sample 1) permits determination of a full-scale image size associated with the signal. For example, for a linear scan at a constant scan velocity, the full-scale image size associated with the signal would be the time of the scan multiplied by the scan rate.

Whenever electron beam 4 passes over a sudden change in elevation on the boundary between a solid portion and a pore space region of sample 1 there will be a sudden change in secondary electron intensity detected by photomultiplier 6, and thus in the voltage output signal generated by photomultiplier 6. Such elevation changes may be determined by differentiating the voltage output signal with respect to time and identifying the changes as the points of zero crossing of the differentiated signal. Signal B of FIG. 2 is such a differentiated signal. Signal B of FIG. 2 is the first time derivative of signal A of FIG. 2. In a preferred embodiment of the invention, A2 signal B is obtained by digitizing signal A in signal digitizer 20 and then numerically computing the derivative of the digitized signal in computer 24. In an alternate preferred embodiment, the unprocessed voltage output signal is digitized, and then simultaneously numerically differentiated and digitally filtered in computer 24 by convolving the digitized signal with the derivative of the impulse response functon of a suitable digital filter. Alternatively, the time derivative of the unprocessed voltage output signal may be computed using known analog techniques.

Graph C of FIG. 2 shows the locations of the zero crossings of signal B of FIG. 2. We identify each pair of adjacent points of zero crossing of the differentiated signal as a "geometric feature" of the sample. The time interval between each pair of adjacent zero crossings is associated with a distance, determinable from the velocity at which electron beam 4 is scanned across sample 1. We define the distance between adjacent zero crossings of the differentiated signal as the "size" of the associated geometric feature.

It is Important to recognize that this definition of a geometric feature does not involve identification of individual solid particles or grains of the sample. Two adjacent points of zero crossing may be associated with relief on the surface of a single particle or the edge of a particle or the boundary between two different solid particles. We view the pore space of the sample as a continuous manifold having shape independent of information about whether or not a geometric feature is part of one particle or part of two or more particles.

In a preferred embodiment, the invention involves generating from the unprocessed voltage output signal A of FIG. 2 a feature size distribution signal indicative of the number of observed geometric features of the sample intersecting the scanning path which have size less than the full-scale image size associated with the unprocessed signal. This preferably is accomplished by differentiating the unprocessed signal to generate the differentiated signal B of FIG. 2, and then computing the distances between adjacent points of zero crossing of the differentiated signal (i.e., computing the sizes of the geometric features detected by the scan). Feature sizes are then sorted with respect to increasing separation between adjacent points of zero crossing. Thus, a feature size distribution is generated from which the number per unit length of detected geometric features having size less than any selected fraction of the full-scale image size may be extracted.

It should be recognized that although we have defined a "geometric feature" of a sample as a pair of adjacent points of zero crossing of a differentiated signal of the type of signal B of figure, we could have alternatively defined "geometric feature" with reference to adjacent points of peak intensity of an election microscope output signal of the type of signal A of FIG. 2. Accordingly in an alternate embodiment of the invention a feature size distribution containing information about a sample's "geometric features", as defined in the alternate manner specified in this paragraph, is generated directly from the unprocessed microscope output signal, without first differentiating such signal with respect to time.

In a preferred embodiment of the invention, the sample is repeatedly imaged with a microscope. On each image, the microscope is operated at a different magnification. A microscope output signal (such as signal A of FIG. 2) associated with a selected magnification is generated for each image. Identical signal processing steps are performed on each of such microscope output signals. It is desirable that the same location on the sample be scanned during each repetition. Alternatively, the sample is imaged once (using a microscope having sufficient resolving capability) to generate a single microscope output signal from which a plurality of feature size distributions signals are generated. In this embodiment, each feature size distribution signal generated from the microscope output signal is indicative of the number of geometric features resolved which have size less than a particular selected size.

It should be recognized that throughout this specification, including the claims, the term "microscope" will be used to denote the broad class of image-forming instruments, including but not limited to all types of microscopes and microdensitometers, which may be used to generate a signal or image of a microporous solid for subsequent processing in accordance with the invention.

Figure 3:
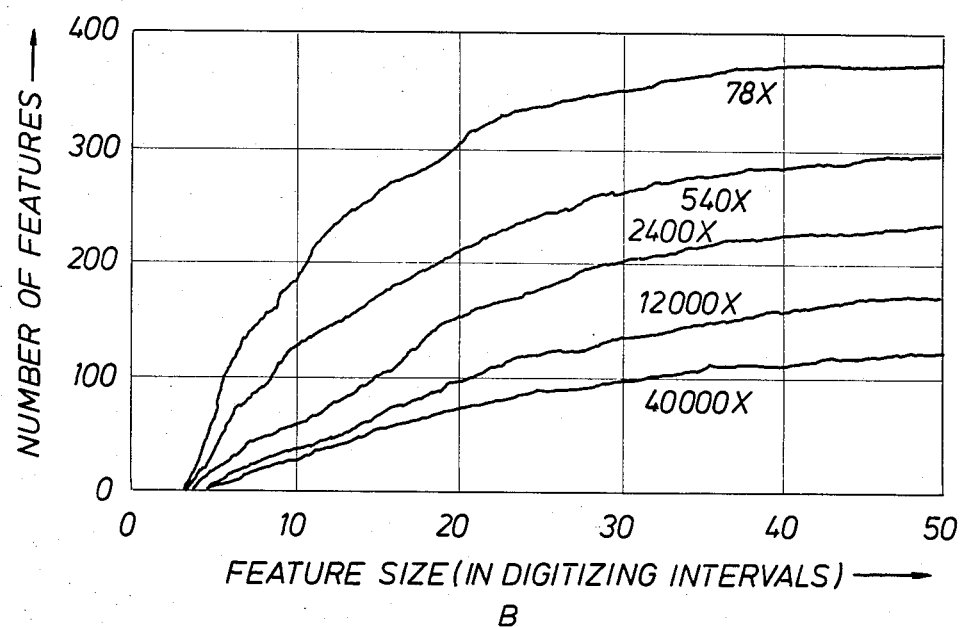
FIG. 3 shows five typical feature size distribution signals, each associated with a different microscope magnification, obtained by scanning a sample of Coconino sandstone (a surface rock originating in Arizona) with a microscope and processing the microscope output signal in accordance with the invention.

FIG. 3 shows five typical feature size distribution signals generated in accordance with the invention by scanning a Coconino sandstone sample with a scanning electron microscope. Each of the five signals was generated from a microscope output voltage signal produced by scanning the sample at a scanning rate having x-component 500 msec. per line and y-component 5 sec. per image. At this scanning rate, the electron beam traced the sample in ten lines. 5120 points of the voltage output signal from each image were digitized. Each signal is associated with an image at a different indicated magnification. For example, the uppermost signal is associated with an image at a magnification of 78× and the lowermost signal is associated with an image at a magnification of 40,000×. Distance away from the horizontal axis represents the number of geometric features identified which have size less than a particular length, l. Distance away from the vertical axis represents the length, l, in units of digitizing intervals (5 sec./5120). The conversion factor between l in units of digitizing intervals and l in units of length depends on the magnification employed, in a manner that will be apparent to those skilled in the art.

It is desirable that the microscope output signal be filtered with a sufficiently low frequency filter to ensure that the resolution of the measuring system is always limited by the filtering process. The measurement resolution function R(l), defined as the probability of detecting a feature of size l given that such a feature exists, will then be a universal function when expressed as a function of a fraction of the full scale size of the image (i.e., $R(l/l^M)$ will be the same function at every magnification where $l^M$ is the full scale image size associated with the magnification M).

One numerical value representing the number of observed geometric features per unit length having size less than a selected length is generated as a result of each scan. Only those features having size sufficiently large to be resolved by the microscope will be observed. Such numerical values (each associated with a different magnification) may be selected by determining, following each repetition of the scanning step, the number of detected features per unit length having size less than the same selected fraction of the full-scale image size associated with the magnification employed during such scan.

Such selected fraction should be chosen to make best use of the statistics of counting all the features detected in a scan. For typical feature size distribution signals as shown in FIG. 3, this criterion would be satisfied by selecting a fraction corresponding to the lowest feature size for all magnifications which marks the edge of the flat upper limit (for large feature sizes) of the signals. Alternatively, the numerical values are determined by performing a log-normal fit to the feature size distribution signals. The log normal fitting procedure has the advantage that for each magnification a unique numerical value is chosen which is determined from the entire feature size distribution signal obtained at such magnification. Alternatively, the numerical values are determined by fitting the feature size distribution signals to a mathematical function that describes the resolution function. In this procedure the mathematical form of the resolution function may be determined from the known properties of the filters used or it may be measured on an image with known statistical properties. This fitting procedure may further use the necessary condition that the total of observed features seen must fill the whole field of view. The latter procedure further has the advantage that a unique numerical value is computed for each magnification and a fractal dimension is obtained at each magnification.

From the numerical values, each representing the number of geometric features per unit length having size less than a selected length which are observed at one of the magnifications employed, the fractal dimensionality, D, of the sample pore space and the maximum and minimum lengths at which the sample exhibits self-similarity are determined. This may be accomplished by drawing a log-log plot of the number of geometric features per unit length having size in the interval between l and $l+\Delta l$ versus the size l. In a preferred embodiment in which the measurement resolution function is independent of magnification, the desired fractal parameters of the sample may be determined from a log-log plot of the difference between the number of geometric features per unit length having size less than a particular length "b", detected at a given magnification and the corresponding number of features per unit length having size less than length "a" detected at a neighboring magnification versus the interval "b-a". A least square fit is made to determine the slope of the region over which the plotted data exhibits linearity. Since the plotted data represent a one dimensional section of the pore space, the slope, s, is identified as s=2-D. The region in which the plotted data exhibits linearity indicates the range of lengths over which the sample exhibits power law behavior and hence, exhibits self-similarity.

Figure 4:
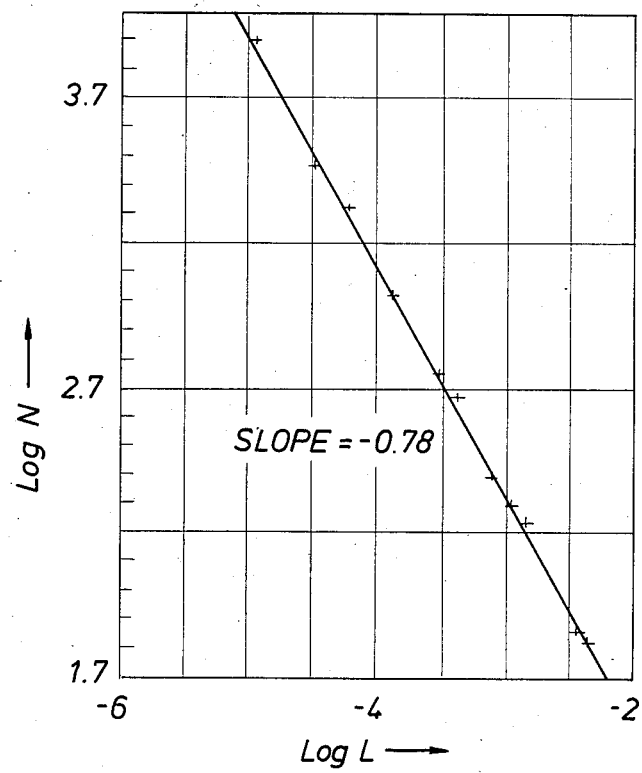
FIG. 4 is a log-log plot of the number of geometric features of size L per unit length versus the size L determined by scanning the cleaved surface of a Coconino sandstone sample with a scanning electron microscope using a range of magnifications from $30\times$ to $60,000\times$.

FIG. 4 is a plot of data generated in accordance with the invention by repeatedly scanning the cleaved surface of a Coconino sandstone sample with a scanning electron microscope using a range of magnifications from 30X to 60,000X. The vertical coordinate of the plotted data represents Log (N), where N is the measured number of geometric features of size L per unit length. The horizontal coordinate of the plotted data represents Log (L), where L is the feature size. As can be seen, the data are linear over the measured range. The slope of the measured data is −0.78, indicating that the fractal dimension of the sample pore space is 2.78.

When a sufficient number of scans of the sample, each using a microscope operated at a different selected magnification, is performed to delineate the upper and lower bounds on the range of feature sizes between which the plotted data exhibits linearity, such upper bound is identified as the maximum length, $l_2$, at which the sample exhibits self-similarity. The lower bound is identified as the minimum length, $l_1$, at which the sample exhibits self-similarity.

In a preferred embodiment of the invention, the minimum magnification at which the sample is scanned is sufficiently low to generate data about sufficiently large features so that the maximum self-similarity length, $l_2$, may be identified from the measured data. Similarly, in a preferred embodiment, the maximum magnification at which the sample is scanned is sufficently high to generate data about sufficiently small features so that the minimum self-similarity length, $l_1$, may be identified from the measured data. It is also within the scope of the invention to perform the above-described technique on a microporous solid to determine only the fractal dimensionality, D, of the solid, where the maximum and minimum self-similarity lengths have been previously determined. It is also within the scope of the invention to perform the above-described technique on a microporous solid to determine both the fractal dimension of the solid, and the maximum self-similarity length, where the minimum self-similarity length has been previously determined. As discussed above, having determined the fractal dimension, D, and the maximum and minimum self-similarity lengths, $l_2$ and $l_1$ respectively, the porosity is determined by the relation $\phi=(l_1/l_2)^{3-D}$.

The procedure described above for determining the fractal dimension and maximum and minimum lengths at which the sample exhibits self-similarity may be performed automatically by processing the feature distribution signals in computer 24 of FIG. 1. To accomplish this, the procedure is translated into a series of computer instructions in a manner that will be apparent to those ordinarily skilled in the art of computer programming. Alternatively, the procedure may be performed manually, on the feature size distribution signals generated according to the invention.

It may be desirable in analyzing certain solids according to the invention to employ both a scanning electron microscope (for measurement of the solid at high magnifications) and an optical microscope (for measurements of the solid at low magnifications). Alternate embodiments of the method described above, particularly suitable when an optical microscope is employed, will be described below in detail. Optical microscope measurements may be required to determine the maximum length at which certain solids exhibit self-similarity.

Figure 5:
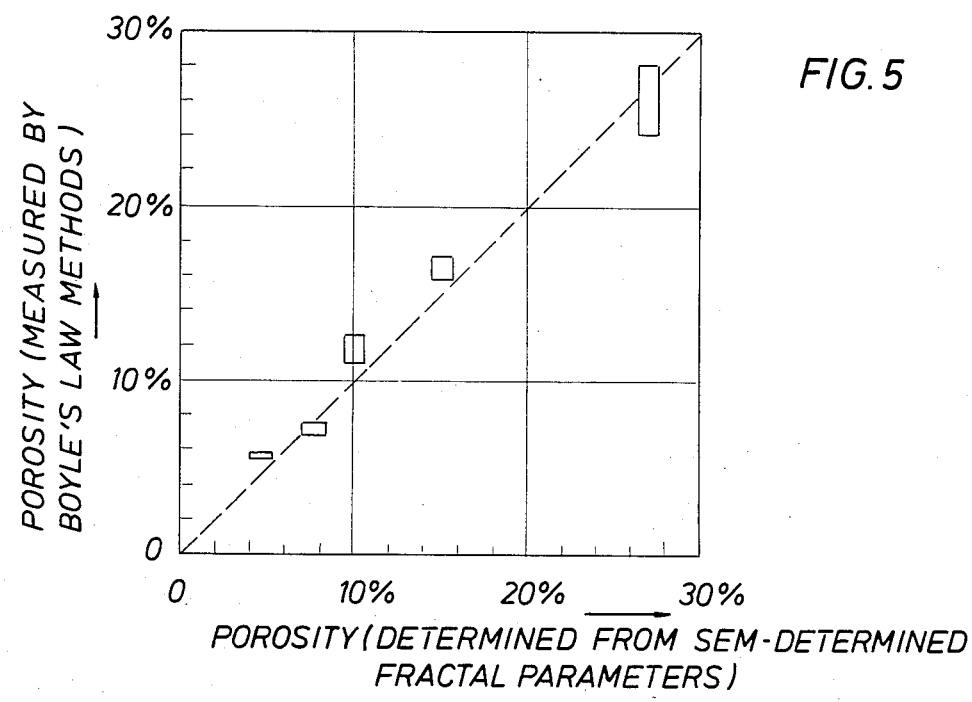
FIG. 5 is a plot of the porosities of five sandstones measured by Boyle's Law methods compared to the porosities determined by performing the method of the invention on the sandstones.

FIG. 5 is a plot of the porosities of five sandstones measured by conventional Boyle's law methods compared with the porosities of the sandstones as determined by performing the method of the invention on the sandstones. In performing the invention on the sandstones, a scanning electron microscope or both a scanning electron microscope (for high magnifications) and an optical microscope (for lower magnifications) were used to scan the sandstone repeatedly, at a plurality of different magnifications. The fractal parameters were determined by processing the resulting microscope output signals. The sandstones measured (in order of increasing porosity) were: a tight gas sand having permeability equal to 0.06 miliDarcy, a tight gas sand having permeability in the range from 0.495 miliDarcy to 0.589 miliDarcy, Coconino sandstone, Navajo sandstone, and St. Peter's sandstone.

Additional physical properties of a microporous solid may be predicted according to the invention by determining additional geometric statistical information regarding the clustering of geometric features of the solid. For example, prediction of the electrical conductivity of a microporous solid (the solid portion of which is substantially electrically insulating) requires additional information about the clustering of geometric features. The reason that such additional information is required may be understood by recognizing that if small features are clustered in constrictions of the pore volume then these features will have a particularly effective role in determining the conductivity. For an ideally nonclustered feature distribution, the volume available to a scattering ion at each length or volume scale is a maximum. When the features cluster, the volume available to an ion will depend on the volume available for a cluster at each length scale. Reducing the available volume reduces the conductivity.

We have found that by determining the clustering statistic, $\gamma$ (defined above), associated with a solid, additional properties of the solid (such as conductivity) may be predicted. The clustering statistic is determined by performing additional signal processing on microscope output signals generated by scanning a sample of the solid at each of a number of different magnifications as previously described. The geometric features of the sample along the scanning path are identified from the microscope output signals. For each microscope output signal, a feature size, $l_M$, not greater than the full scale image size associated with the magnification, M, employed in generating the microscope output signal, is selected. The average cluster size containing the detected features of size less than $l_M$ is then determined. We unambiguously identify all "clusters" of features having size less than $l_M$ as follows. We identify all features having size less than $l_M$. For each such identified feature, F, we identify the largest collection of features which includes feature F and which has the properties that each feature in the collection is adjacent to one other feature in the collection, and that each feature in the collection has size less than $l_M$. Each one of such distinct collections is identified as a "cluster" of detected features having size less than $l_M$. The average size of all clusters of detected features having size less than a selected size is determined at each magnification.

Having determined the average cluster size, $l^M_{cluster}$, associated with each of the microscope output signals (each of which is associated with a different magnification, M), we determine the reduced volume, $V^M_{reduced} = (l^M_{cluster}/l_1)^D$, associated with each average cluster size, where $l_1$ is the minimum length at which the solid exhibits self-similarity.

Figure 6:
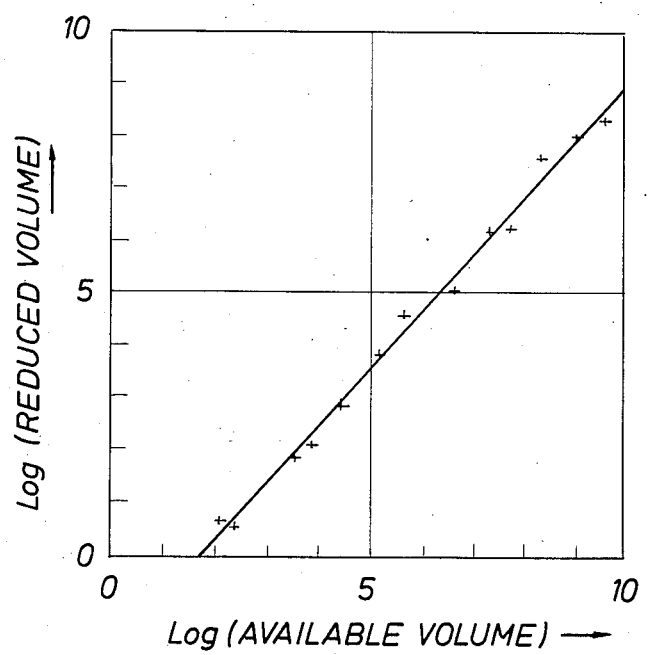
FIG. 6 is a log-log plot of the measured reduced volume occupied by geometric features of size $l_M$, versus the available volume in the absence of clustering, determined from a Coconino sandstone sample.

We then plot log $V^M_{reduced}$ versus log $(l_M/l_1)^D$ for each selected feature size $l_M$. FIG. 6 shows such a plot, generated from data obtained using a scanning electron microscope to measure the geometric features of a cleaved surface of a Coconino sandstone sample. The quantity $(l_M/l_1)^D$ is referred to in FIG. 6, and elsewhere herein, as the "available volume". Defining the horizontal axis of FIG. 6 as the "x" axis, we identify the x-coordinate of the point of intersection of the data with the "x" axis as $-\gamma \log (l_1/l_2)$, where $l_1$ and $l_2$ are the minimum and maximum lengths at which the solid exhibits self-similarity and $\gamma$ is the clustering statistic.

Having determined the clustering statistic, $\gamma$, in the manner described above, the electrical conductivity of the measured sample is determined from the relation: $\sigma = \sigma_s + \sigma_w(l_1/l_2)^{3-D+\gamma}$, where $\sigma_w$ is the electrical conductivity of fluid saturating the pore space, $\sigma_s$ is the electrical conductivity of the solid portion of the porous sample, D is the measured fractal dimensionality, and $l_1$ and $l_2$ respectively are the minimum and maximum lengths at which the sample exhibits self-similarity. The quantity $\sigma_s$ will be non-zero for rocks having electrically conducting grains, such as clays or pyrite.

Those of ordinary skill in the art will recognize that in the general case, porous solids hving electrically conducting solid portions must be treated as highly complex interconnected materials and that specialized theories have been developed to model such materials. As an example, I. Webman et al., in "Numerical Simulation of Electrical Conductivity in Microscopically Inhomogeneous Materials", Physical Review B, 11, pp. 2885-2891 (1975), have applied effective media models to simulate the conductitivy of inhomogeneous materials. Such models are needed to model the conductivity of an electrically conducting solid-fluid composite. The relation set forth above for the electrical conductivity of such a composite is the result of one such model. It is recognized that alternate models may be applied to generate alternate expressions of such electrical conductivity in which $\sigma_s$ and $\sigma_w$ are combined differently, but, which reduce to the same expression as does the relation set forth above in the case that $\sigma_s$ is zero.

In a preferred embodiment of the invention, the fractal parameters of the sample are extracted from feature size distribution signals generated by processing the digitized signal from signal digitizer 20. To accomplish this, the above-described procedure for determining D, $l_1$, $l_2$, and $\gamma$ is translated into a series of computer instructions in a manner that will be apparent to those ordinarily skilled in the art of computer programming.

Alternatively, the desired fractal parameters may be extracted from feature size distribution signals obtained by generating at each magnification a voltage output signal of the type shown as signal A in FIG. 2, and thereafter applying analog signal processing techniques to such signals. Such voltage output signals are time-dependent. The time between relative voltage peaks is proportional to the distance between geometric features of the measured sample. We analyze the frequency or time domain content of the signals to obtain the distribution of geometric feature sizes at each magnification. By applying a narrow filter at frequency $\omega_o$ to each voltage output signal, we obtain filtered signals at each magnitude having amplitude which corresponds to the intensity-weighted number of features having a time separation of $1/\omega_o$. When $\omega_o$ and the full scale scan rates are held constant at each magnification the distance corresponding to $\omega_o$ is a constant fraction of the full scale image and scales with magnification. A log-log plot of filtered intensity versus (magnification)$^{-1}$ will then facilitate determination of desired fractal parameters.

Direct analysis of the analog signals by filtering or by spectrum analysis convolutes intensity and number information. In order for the filtered signal to be proportional to the number of events (cycles) of frequency $\omega_o$ at all magnifications, the amplitude of the signals of frequency $\omega_o$ have to be the same at all magnifications. Alternatively, the signal at $\omega_o$ has to be properly normalized by the average intensity. This normalization is made with respect to the rms value of the intensity of the voltage output signal over a bandwidth corresponding to the lengths lying between the full scale length of the image and the resolution limit on the image.

Figure 7:
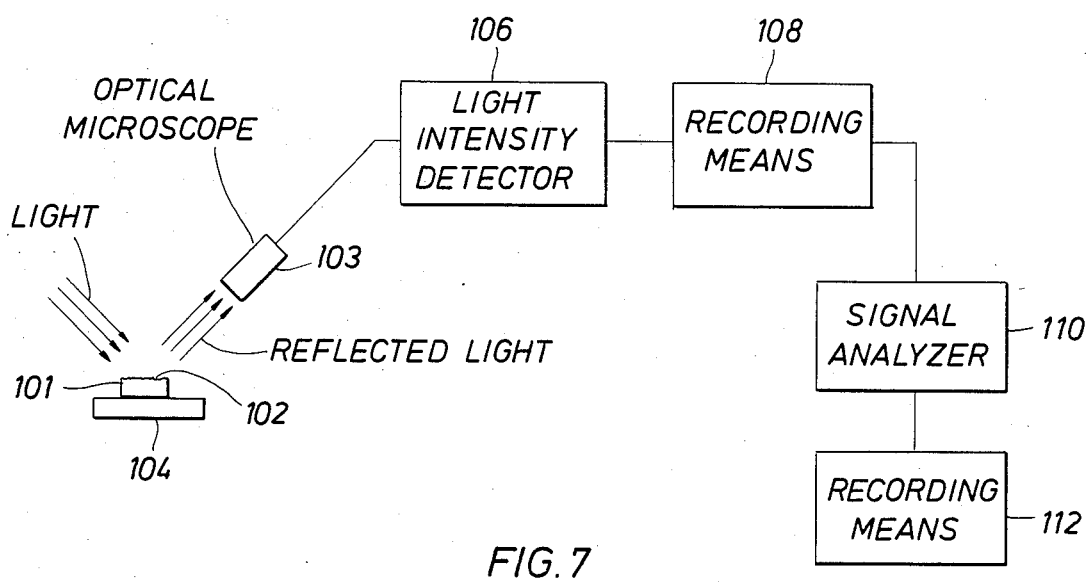
FIG. 7 is a schematic diagram of an alternate embodiment of the automated measurement system of the invention which employs an optical microscope or microdensitometer.

In an alternate embodiment, the invention involves measuring the geometric features of a microporous solid (such as a microporous rock) using an optical microscope. Such embodiment may be understood with reference to FIG. 7. Sample 101 of the solid having fracture surface 102 is mounted on mobile stage 104. Fracture surface 102 is illuminated and light reflected therefrom is magnified by means of optical microscope 103. Optical microscope 103 is preferably operable at several different magnifications. A suitable optical microscope may be selected from those commercially available. By moving mobile stage 104, the sample is moved relative to microscope 103. As the stage is moved, a microscope output signal is generatd. The microscope output signal is indicative of variations in light intensity reflected from the fracture surface. The intensity of the output signal is then measured using light intensity detector 106. A suitable light intensity detector such as a photomultiplier tube or a semiconductor diode may be selected from those commercially available. As sample 101 is translated or rotated using mobile stage 104 the output of light intensity detector 106 is recorded in recording means 108. Suitable recording means may be selected from those commercially available. Variations in intensity occur because of variations in color on the sample surface but more importantly because geometric structure on the surface causes shadows in the neighborhood of geometric features. The spatially-dependent reflected optical intensity is then a measure of spatial variations in structure on which geometric features can be identified.

Those ordinarily skilled in the art will recognize that an optical microscope operated in the above mode of operation is similar to commercially available instruments known as microdensitometers. Such special purpose instruments, selected from those commercially available having suitable resolution and measurement capabilities, may be substituted for the more generally useful microscope 103 in the system of FIG. 7. Throughout this specification, and in the claims, the phrase "optical microscope" will be used to denote the class of image-forming instruments which includes optical microscopes and microdensitometers.

The signals recorded in recording means 108 are analyzed in signal analyzer 110. Recording means 112 is connected to signal analyzer 110 to record the output thereof. Signal analyzer 110 desirably includes a signal digitizer and a computer. We have found that a Hewlett-Packard Model 5420 Signal Analyzer or a Hewlett-Packard HP-3437A voltmeter coupled with a Tektronics 4054 computer is suitable. Suitable recording means may be selected from those commercially available. Geometric features are defined, as defined as above with reference to FIG. 1, to be the points of zero crossing of the spatial derivative of the reflected light intensity. By repeatedly scanning fracture surface 102 at different magnifications (or by scanning the sample surface a single time at a high resolution) and processing the signals recorded in recording means 108 in the same manner as in the scanning electron microscope techniques discussed above, the desired fractal parameters of the sample are determined.

In an alternate preferred embodiment of the invention, geometric features of a microporous solid are measured on transparent thin sections of the solid. The methods for preparation of transparent thin sections of porous media are well known to those skilled in the art of petrophysics. On thin sections, pore space can be uniquely labeled by, for example, injection of colored bonders or fluorescent material in the pore space. Those skilled in the art will also recognize that optical photographs and electron microscope images of thin sections can be made such that solid matter comprising the sample is identified separately from pore space material. For example, digital computers can be programmed to recognize the color in pore space filling material. In one embodiment, a scanning electron microscope is used in a back-scattered electron mode to distinguish solid and pore spaces. Alternatively, an optical microscope is used to detect the fluorescent nature of pore space material. Images of thin sections or thin sections themselves may then be used to obtain an optical image of the pore space in a porous media.

In this alternate preferred embodiment, an optical image (such as a pore space enhanced photograph of a thin section) is prepared and then used to extract fractal parameters. The optical image may be obtained by any means known in the art. We shall describe below a preferred embodiment of the method in which a pore space enhanced photograph is prepared and used to extract fractal parameters. It should be understood that the technique described below is also applicable to extract fractal parameters from other types of optical images of thin sections. The pore-enhanced photograph is examined using an optical microscope in transmitted or reflected light. A system of the type described above with reference to FIG. 7 may be used to examine such a photograph in reflected light (and extract the fractal parameters of interest), in which case the photograph would be positioned on mobile stage 104 in place of sample 101. An arbitrary origin on the photograph is chosen, the photograph is moved relative to the microscope and the magnified optical image passed contemporaneously through an aperture (not shown in FIG. 7). A microdensitometer selected from those commercially available having a variable aperture may be used to examine the photograph, rather than an optical microscope with a variable aperture. The spatially-dependent light intensity transmitted through the aperture is measured in the same manner as is the reflected light intensity from fracture surface 102 in the alternate embodiment discussed above with reference to FIG. 7. The size of the aperture is changed and the steps of translating the photograph relative to the microscope and recording the transmitted spatially dependent optical intensity signal are repeated.

It is desirable that the aperture have variable radius. A sufficient number of repetitions should be performed so that apertures having size in a sufficiently broad range are employed to permit determination of the desired fractal parameters. Between each repetition of the translation step, the origin of the photograph is returned to its original position relative to the microscope.

The measured intensity of light transmitted through the aperture is an averaged intensity proportional to the ratio of the area of pore space to the area of solid material in the portion of the photograph observed through the aperture. By plotting the log of the measured averaged intensity versus the log of the aperture size, the fractal dimension, D, of the measured solid is determined in a manner analogous to the manner (discussed above) in which the fractal dimension is determined from feature size distribution signals resulting from scanning electron microscope measurements. The maximum self-similarity length $l_2$ is identified as the size of the smallest aperture at which translation causes no systematic changes in measured averaged intensity (i.e. at which the measured averaged intensity signal, normalized by the area of the aperture through which the intensity is measured, has form independent of the aperture size used). Length $l_2$ is the length above which the geometry is homogeneous. For apertures smaller than $l_2$ the measured light intensity is not proportional to the area of the aperture. In the length scale region smaller than $l_2$ the variation of intensity with aperture diameter is used to determine the fractal dimension.

In a variation of this technique the fractal dimension associated with a microporous rock sample is determined by sequentially scanning a photographic image of a thin section of the rock sample using an aperture (in a microscope or microdensitometer) having size comparable to or smaller than the smallest structure observed on the thin section. The detected light intensity is a maximum when the aperture is over pore space and a minimum when over grain space. The fractal dimension is determined by counting the number of length segments in pore space having length of a particular size in a manner similar to that described above with reference to FIG. 2. The distribution of the number of pore segments of size l is used to determine the fractal dimension by plotting the logarithm of the number of segments versus the logarithm of the length of the segment. The slope of the log-log plot is 2-D, where D is the fractal dimension.

The above description is merely illustrative of the present invention. Various changes in details of methods and apparatus described may be within the scope of the appended claims without departing from the spirit of the invention.

We claim as our invention:

1. A method for determining pore-dependent properties of a microporous solid, comprising the steps of:
    (a) scanning the surface of a sample of the solid with a microscope operated at a first selected magnification to generate a microscope output signal indicative of geometric features of the sample intersecting a path on the surface;
    (b) generating from the microscope output signal a feature size distribution signal indicative of the number of geometric features resolved by the microscope which intersect the path and which have size less than a selected fraction of the full-scale image size associated with said first selected magnification;
    (c) repeating steps (a) and (b), operating the microscope used during each repetition at a selected magnification different from each magnification used in performing a previous repetition so as to generate during each repetition a microscope output signal associated with the selected magnification used during such repetition and a feature size distribution signal associated with the selected magnification used during such repetition; and
    (d) determining from the generated feature size distribution signals the fractal dimensionality, D, of the sample pore space, from which the porosity, $\phi$, is determined by the relation $\phi=(l_1/l_2)^{3-D}$, where $l_1$ is the minimum length at which the sample exhibits self-similarity and $l_2$ is the maximum length at which the sample exhibits self-similarity.

2. The method of claim 1, also including the step of: determining from the generated feature size distribution signals the clustering statistic, $\gamma$, associated with the sample pore space, from which the solid electrical conductivity, $\sigma$, is determined.

3. The method of claim 1, also including the step of: determining from the generated feature size distribution signals the clustering statistic, $\gamma$, associated with the sample pore space, from which the solid electrical conductivity, $\sigma$, is determined by the relation $\sigma=\sigma_s+\sigma_w(l_1/l_2)^{3-D+\gamma}$, where $\sigma_w$ is the electrical conductivity of fluid saturating the pore space, and $\sigma_s$ is the electrical conductivity of the solid in the absence of electrically conductive material in the pore space of the solid.

4. The method of claim 1 wherein the solid portion of the microporous solid is electrically insulating, and also including the step of: determining from the generated feature size distribution signals the clustering statistic, $\gamma$, associated with the sample pore space, from which the solid electrical conductivity, $\sigma$, is determined by the relation $\sigma=\sigma_w(l_1/l_2)^{3-D+\gamma}$, where $\sigma_w$ is the electrical conductivity of fluid saturating the pore space.

5. The method of claim 1 wherein steps (a) and (b) are repeated until a sufficient range of microscope magnifications has been used so that the generated feature size distribution signals may be analyzed to permit approximate determination of the maximum length at which the sample exhibits self-similarity, and also including the step of: determining from the generated feature size distribution signals the maximum length, $l_2$, at which the sample exhibits self-similarity.

6. The method of claim 5 wherein steps (a) and (b) are repeated until a sufficient range of microscope magnifications has been used so that the generated feature size distribution signals may be analyzed to permit approximate determination of the minimum length at which the sample exhibits self-similarity, and also including the step of: determining from the generated feature size distribution signals the minimum length, $l_1$, at which the sample exhibits self-similarity.

7. The method of claim 1 wherein:
    the feature size distribution signal is generated by generating a differentiated signal whose magnitude is substantially equal to the magnitude of the time derivative of the microscope output signal; and
    the feature size distribution signal is indicative of the number distribution of spacings between adjacent zero-crossings of the differentiated signal as a function of the length of such spacings.

8. The method of claim 7 wherein:
    the differentiated signal is generated by digitizing the microscope output signal and then numerically computing the time derivative of the digitized signal.

9. The method of claim 8 also including the step of: filtering the microscope output signal through a low pass filter having linear phase and a non-oscillating impulse response function prior to digitizing the microscope output signal.

10. A method for determining pore-dependent properties of a microporous rock, comprising the steps of:

(a) scanning the surface of a sample of the rock with a microscope operated at a first selected magnification to generate a microscope output signal indicative of geometric features of the sample intersecting a path on the surface;

(b) generating from the microscope output signal a feature size distribution signal indicative of the number of geometric features resolved by the microscope which intersect the path and which have size less than a selected fraction of the full-scale image size associated with said first selected magnification;

(c) repeating steps (a) and (b), operating the microscope used during each repetition at a selected magnification different from each magnification used in performing a previous repetition so as to generate during each repetition a microscope output signal associated with the selected magnification used during such repetition and a feature size distribution signal associated with the selected magnification used during such repetition; and (d) determining from the generated feature size distribution signals the fractal dimensionality, D, of the sample pore space, from which the rock porosity, $\phi$, is determined by the relation $\phi = (l_1/l_2)^{3-D}$, where $l_1$ is the minimum length at which the sample exhibits self-similarity and $l_2$ is the maximum length at which the sample exhibits self-similarity.

11. The method of claim 10, also including the step of:
determining from the generated feature size distribution signals the clustering statistic, $\gamma$, associated with the sample pore space, from which the rock electrical conductivity, $\sigma$, is determined.

12. The method of claim 10 also including the step of:
determining from the generated feature size distribution signals the clustering statistic, $\gamma$, associated with the sample pore space, from which the rock electrical conductivity, $\sigma$, is determined by the relation $\sigma = \sigma_s + \sigma_w(l_1/l_2)^{3-D+\gamma}$, where $\sigma_w$ is the electrical conductivity of fluid saturating the pore space, and $\sigma_s$ is the electrical conductivity of the rock in the absence of electrically conductive material in the pore space of the rock.

13. The method of claim 10 wherein the rock portion of the microporous rock is electrically insulating, and also including the step of:
determining from the generated feature size distribution signals the clustering statistic, $\gamma$, associated with the sample pore space, from which the rock electrical conductivity, $\sigma$, is determined by the relation $\sigma = \sigma_w(l_1/l_2)^{3-D+\gamma}$, where $\sigma_w$ is the electrical conductivity of fluid saturating the pore space.

14. The method of claim 10 wherein steps (a) and (b) are repeated until a sufficient range of microscope magnifications has been used so that the generated feature size distribution signals may be analyzed to permit approximate determination of the maximum lenth at which the sample exhibits self-similarity, and also including the step of:
determining from the generated feature size distribution signals the maximum length, $l_1$, at which the sample exhibits self-similarity.

15. The method of claim 14 wherein steps (a) and (b) are repeated until a sufficient range of microscope magnifications has been used so that the generated feature size distribution signals may be analyzed to permit approximate determination of the minimum length at which the sample exhibits self-similarity, and also including the step of:
determining from the generated feature size distribution signals the minimum length, $l_1$, at which the sample exhibits self-similarity.

16. The method of claim 10 wherein:
the feature size distribution signal is generated by generating a differentiated signal whose magnitude is substantially equal to the magnitude of the time derivative of the microscope output signal; and
the feature size distribution signal is indicative of the number distribution of spacings between adjacent zero-crossings of the differentiated signal as a function of the length of such spacings.

17. The method of claim 16 wherein:
the differentiated signal is generated by digitizing the microscope output signal and then numerically computing the time derivative of the digitized signal.

18. The method of claim 17 also including the step of:
filtering the microscope output signal through a low pass filter having linear phase and a non-oscillating impulse response function prior to digitizing the microscope output signal.

19. A method for determining pore-dependent properties of a microporous solid, comprising the steps of:
(a) translating an electron beam of a scanning electron microscope operated at a first selected magnification through a path adjacent to a sample of the solid to produce a voltage signal indicative of geometric features of the sample intersecting the projection of the path on the sample;

(b) generating from the voltage signal a feature size distribution signal indicative of the number of geometric features resolved by the microscope which intersect the path and which have size less than a selected fraction of the full-scale image size associated with said first selected magnification;

(c) repeating steps (a) and (b), operating the scanning electron microscope during each repetition at a selected magnification different from each magnification used in performing a previous repetition so as to generate during each repetition a voltage signal associated with the selected magnification used during such repetition and a feature size distribution signal associated with the selected magnification used during such repetition, until a sufficient range of magnifications has been used so that the generated feature size distribution signals may be analyzed to determine approximately the maximum length at which the sample exhibits self-similarity; and (d) determining from the generated feature size distribution signals the fractal dimensionality, D, of the sample pore space and the maximum length, $l_2$, at which the sample exhibits self-similarity, from which the porosity, $\phi$, is determined by the relation $\phi = (l_1/l_2)^{3-D}$, where $l_1$ is the minimum length at which the sample exhibits self-similarity.

20. The method of claim 19 wherein steps (a) and (b) are repeated until a sufficient range of microscope magnifications has been used so that the generated feature size distribution signals may be analyzed to permit approximate determination of both the maximum and minimum lengths at which the sample exhibits self-similarity, and also including the step of:

determining from the generated feature size distribution signals the minimum length at which the sample exhibits self-similarity.

21. The method of claim 19, also including the step of: determining from the generated feature size distribution signals the clustering statistic, $\gamma$, associated with the sample pore space, from which the solid electrical conductivity, $\sigma$, is determined.

22. The method of claim 19 also including the step of: determining from the generated feature size distribution signals the clustering statistic, $\gamma$, associated with the sample pore space, from which the solid electrical conductivity, $\sigma$, is determined by the relation $\sigma = \sigma_s + \sigma_w(l_1/l_2)^{3-D+\gamma}$, where $\sigma_w$ is the electrical conductivity of fluid saturating the pore space, and $\sigma_s$ is the electrical conductivity of the solid in the absence of electrically conductive material in the pore space of the solid.

23. The method of claim 19 wherein the solid portion of the microporous solid is electrically insulating, and also including the step of: determining from the generated feature size distribution signals the clustering statistic, $\gamma$, associated with the sample pore space, from which the solid electrical conductivity, $\sigma$, is determined by the relation $\sigma = \sigma_w(l_1/l_2)^{3-D+\gamma}$, where $\sigma_w$ is the electrical conductivity of fluid saturating the pore space.

24. The method of claim 19 wherein the sample is a portion of the solid having a fracture surface, and the voltage signal is indicative of geometric features intersecting the projection of the path on the fracture surface of the sample.

25. The method of claim 19 wherein:
the feature size distribution signal is generated by generating a differentiated signal whose magnitude is substantially equal to the magnitude of the time derivative of the voltage signal; and
the feature size distribution signal is indicative of the number distribution of spacings between adjacent zero-crossings of the differentiated signal as a function of the length of such spacings.

26. The method of claim 25 wherein:
the differentiated signal is generated by digitizing the voltage signal and then numerically computing the time derivative of the digitized signal.

27. A method for determining pore-dependent properties of a microporous solid, comprising the steps of:
(a) scanning the surface of a sample of the solid with a microscope operated at a selected magnification to generate a microscope output signal indicative of geometric features of the sample intersecting a path on the surface;
(b) generating from the microscope output signal a feature size distribution signal indicative of the number of geometric features resolved by the microscope which intersect the path and which have size less than a selected maximum size;
(c) repeating step (b) generating during each repetition a feature size distribution signal associated with a selected maximum feature size different from each maximum size selected in performing a previous repetition; and
(d) determining from the generated feature size distribution signals the fractal dimensionality, D, of the sample pore space, from which the porosity, $\phi$, is determined by the relation $\phi = (l_1/l_2)^{3-D}$, where $l_1$ is the minimum length at which the sample exhibits self-similarity and $l_2$ is the maximum length at which the sample exhibits self-similarity.

28. The method of claim 27, also including the step of: determining from the generated feature size distribution signals the clustering statistic, $\gamma$, associated with the sample pore space, from which the solid electrical conductivity, $\sigma$, is determined.

29. The method of claim 27, also including the step of: determining from the generated feature size distribution signals the clustering statistic, $\gamma$, associated with the sample pore space, from which the solid electrical conductivity, $\sigma$, is determined by the relation $\sigma = \sigma_s + \sigma_w(l_1/l_2)^{3-D+\gamma}$, where $\sigma_w$ is the electrical conductivity of fluid saturating the pore space, and $\sigma_s$ is the electrical conductivity of the solid in the absence of electrically conductive material in the pore space of the solid.

30. The method of claim 27 wherein the solid portion of the microporous solid is electrically insulating, and also including the step of: determining from the generated feature size distribution signals the clustering statistic, $\gamma$, associated with the sample pore space, from which the solid electrical conductivity, $\sigma$, is determined by the relation $\sigma = \sigma_w(l_1/l_2)^{3-D+\gamma}$, where $\sigma_w$ is the electrical conductivity of fluid saturating the pore space.

31. The method of claim 27 wherein step (b) is repeated until a sufficient number of feature size distribution signals has been generated so that the generated feature size distribution signals may be analyzed to permit approximate determination of the maximum length at which the sample exhibits self-similarity, and also including the step of: determining from the generated feature size distribution signals the maximum length, $l_2$, at which the sample exhibits self-similarity.

32. The method of claim 31 wherein step (b) is repeated until a sufficient number of feature size distribution signals has been generated so that the generated feature size distribution signals may be analyzed to permit approximate determination of the minimum length at which the sample exhibits self-similarity, and also including the step of: determining from the generated feature size distribution signals the minimum length, $l_1$, at which the sample exhibits self-similarity.

33. A method for determining pore-dependent properties of a microporous solid, comprising the steps of:
(a) mounting a sample of the solid on a mobile stage, said sample having a fracture surface;
(b) illuminating the fracture surface and magnifying light reflected from the fracture surface using an optical microscope operated at a first selected magnification;
(c) moving the mobile stage along a path relative to the optical microscope and contemporaneously generating a microscope output signal indicative of variations in light intensity reflected from the fracture surface and magnified by the microscope operated at said first selected magnification;
(d) recording the microscope output signal associated with said first selected magnification;
(e) repeating steps (b), (c), and (d), operating the optical microscope during each repetition at a selected magnification different from each magnification used in performing a previous repetition so as to generate during each repetition a microscope output signal associated with the selected magnification used during such repetition, until a sufficient number of microscope output signals, each associated with a different magnification, are recorded so that the recorded signals may be analyzed to determine approximately the maximum length at which the sample exhibits self-similarity; and (f) determining from the recorded signals the fractal dimensionality, D, of the sample pore space, the maximum length, $l_2$, at which the sample exhibits self-similarity, and the sample porosity, $\phi$, where $\phi = (l_1/l_2)^{3-D}$, where $l_1$ is the minimum length at which the sample exhibits self-similarity.

34. The method of claim 33 also including the step of: determining from the recorded signals the clustering statistic, $\gamma$, associated with the sample pore space, from which the solid's electrical conductivity, $\sigma$, is determined.

35. The method of claim 33 also including the step of: determining from the recorded signals the clustering statistic, $\gamma$, associated with the sample pore space, from which the solid's electrical conductivity, $\sigma$, is determined by the relation $\sigma = \sigma_s + \sigma_w (l_1/l_2)^{3-D+\gamma}$, where $\sigma_w$ is the electrical conductivity of fluid saturating the pore space, and $\sigma_s$ is the electrical conductivity of the solid in the absence of electrically conductive material in the pore space of the solid.

36. The method of claim 33 wherein the solid portion of the microporous solid is electrically insulating, and also including the step of:
determining from the generated feature size distribution signals the clustering statistic, $\gamma$, associated with the sample pore space, from which the solid electrical conductivity, $\sigma$, is determined by the relation $\sigma = \sigma_w (l_1/l_2)^{3-D+\gamma}$, where $\sigma_w$ is the electrical conductivity of fluid saturating the pore space.

37. A method for determining pore-dependent properties of a microporous solid comprising the steps of:
(a) preparing a transparent thin section of the solid;
(b) generating from the thin section a magnified optical image indicative of geometric features of the thin section;
(c) illuminating the optical image;
(d) contemporaneously translating the optical image relative to a member having an aperture having a first aperture size, so that the intensity of a portion of the optical image is measurable through the aperture;
(e) contemporaneously generating an image intensity signal indicative of the spatial dependence of the optical image intensity measured through the aperture as the optical image is translated relative to the aperture;
(f) repeating steps (d) and (e), translating the optical image during each repetition relative to a member having an aperture having an aperture size different from that of each aperture associated with an image intensity signal generated during a previous repetition, until a sufficient range of aperture sizes has been used so that the generated image intensity signals may be analyzed to determine approximately the maximum length at which the sample exhibits self-similarity; and
(g) determining from the generated image intensity signals the fractal dimensionality, D, of the sample pore space and the maximum length, $l_2$, at which the sample exhibits self-similarity from which the porosity, $\phi$, is determined by the relation $\phi = (l_1/l_2)^{3-D}$, where $l_1$ is the minimum length at which the sample exhibits self-similarity.

38. The method of claim 37 wherein the optical image is a pore space enhanced photograph.

39. The method of claim 37 wherein the optical image is a pore space enhanced photograph generated from the voltage output of a scanning electron microscope operated in a back-scattered electron mode.

40. A system for determining pore-dependent properties of a microporous solid sample by performing substantially identical processing on measured data indicative of microscopic geometric features of the sample, comprising:
(a) a microscope, for producing microscope output signals such that each microscope output signal is associated with a different magnification, where each magnification is associated with a different full-scale image size;
(b) a low-pass anti-aliasing filter connected to the microscope for filtering each microscope output signal, said filter having linear phase and a non-oscillating response function;
(c) a signal digitizer connected to the anti-aliasing filter, for digitizing each microscope output signal after it is filtered by the anti-aliasing filter; and
(d) means for generating a feature size distribution signal from each digitized microscope output signal, so that each of said feature size distribution signals is indicative of the number of geometric features intersecting a path on the sample and having size less than a selected fraction of the full-scale image size associated with the magnification associated with said feature size distribution signal.

41. The system of claim 40, also comprising:
means for recording each feature size distribution signal generated by the feature size distribution signal generating means.

42. A system for determining pore-dependent properties of a microporous solid sample by performing substantially identical processing on measured data indicative of microscopic geometric features of the sample, comprising:
(a) a microscope for producing a microscope output signal indicative of geometric features of the sample;
(b) a low-pass anti-aliasing filter connected to the microscope for filtering the microscope output signal, said filter having linear phase and a non-oscillating response function;
(c) a signal digitizer connected to the anti-aliasing filter, for digitizing the microscope output signal after it is filtered by the anti-aliasing filter; and
(d) means for generating a plurality of feature size distribution signals from the digitized microscope output signal, so that each of said feature size distribution signals is indicative of the number of geometric features intersecting a path on the sample and having size less than a selected size.

43. The system of claim 42, also comprising:
means for recording each feature size distribution signal generated by the feature size distribution signal generating means.

* * * * *